United States Patent [19]
Colson et al.

[11] Patent Number: 5,986,107
[45] Date of Patent: Nov. 16, 1999

[54] PROCESS FOR THE PREPARATION OF A 2-OXOPYRROLIDINE COMPOUND

[75] Inventors: Pierre-Jean Colson, Skokie; Kevin A. Babiak, Evanston; Donald E. Korte, Mundelein; Claire A. Przybyla, Des Plaines; Lisa M. Seaney, Glen Ellyn; Bruce E. Wise, Elmhurst, all of Ill.

[73] Assignee: G. D. Searle & Co., Chicago, Ill.

[21] Appl. No.: 09/261,303

[22] Filed: Mar. 2, 1999

Related U.S. Application Data

[60] Provisional application No. 60/081,075, Apr. 8, 1998.
[51] Int. Cl.⁶ .................................................. C07D 207/14
[52] U.S. Cl. .............................................. 548/550
[58] Field of Search ............................................. 548/550

[56] References Cited

U.S. PATENT DOCUMENTS 5,484,946  1/1996  Abood et al. ........................... 548/543

*Primary Examiner*—Johann Richter
*Assistant Examiner*—Dominic Keating
*Attorney, Agent, or Firm*—Cynthia S. Kovacevic

[57] ABSTRACT

A process for producing a lactam of the formula

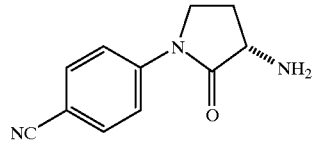

(I)

wherein 2-bromo-4 chloro butyryl bromide or 2,4-dibromo butyryl bromide is coupled with 4-aminobenzonitrile to produce 4-(2,4-bromobutyrylamino)-benzonitrile, which is combined with sodium hydroxide, potassium hydroxide or potassium carbonate to produce 4-(3-bromo-2-oxopyrrolidin-1-yl)benzonitrile which is subjected to an excess of ammonium hydroxide to produce compounds of the formula (I).

1 Claim, No Drawings

PROCESS FOR THE PREPARATION OF A 2-OXOPYRROLIDINE COMPOUND

The present application claims priority under 35 USC §119(e) of United States provisional patent application Ser. No. 60/081,075 filed Apr. 8, 1998.

FIELD OF THE INVENTION

The present invention is directed to a process for the preparation of (3S)-3-amino-1-(4-cyanophenyl)-2-oxopyrrolidine hydrochloride which is useful as an intermediate in the preparation of a GP IIb/IIIa antagonist compound.

BACKGROUND OF THE INVENTION

The invention herein is directed to the preparation of a compound of the formula

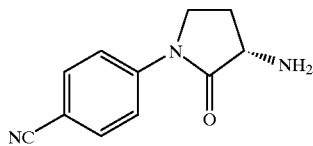

using reagents and reaction conditions which are beneficial in comparison to previously disclosed methodology. This compound is useful in the preparation of the platelet aggregation inhibitor, GP IIb/III antagonist, orbofiban.

Orbofiban is an antiplatelet pharmaceutical agent of the formula

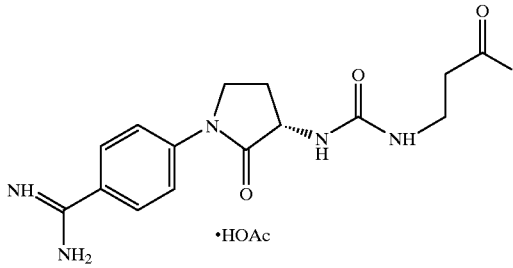

disclosed in U.S. Pat. No. 5,721,366. A process for making orbofiban is disclosed therein.

A process for preparing an intermediate of the formula

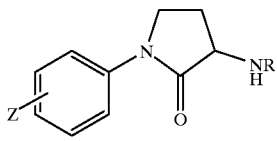

is disclosed in U.S. Pat. No. 5,484,946. It is further disclosed therein that the intermediate is useful in the preparation of ethyl 3-[[[[1-[4-(aminoiminomethyl)phenyl]-2-oxo-3(S)-pyrrolidinyl]amino]carbonyl]amino]-propionate acetate, also known as orbofiban. The process disclosed therein is for producing a lactam of the formula

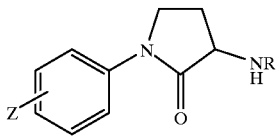

wherein R is a protecting group such as t-butoxycarbonyl (BOC) or carbobenzyloxy (CBZ) and Z is H, —CN, —CONH$_2$ or CO$_2$alkyl from a methionine analog of the formula

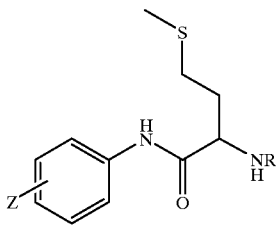

by treating the methionine analog with trimethylsulfonium halide or trimethylsulfoxonium halide (such as trimethylsulfonium iodide or trimethylsulfoxonium chloride) in the presence of an inorganic or aminergic base in a suitable aprotic solvent.

The process disclosed therein further provides for dehydrating the lactam so produced when Z is —CONH$_2$ and deprotecting the lactam, reacting the resulting product with a β-amino ester in the presence of CDI to produce a urea of the formula

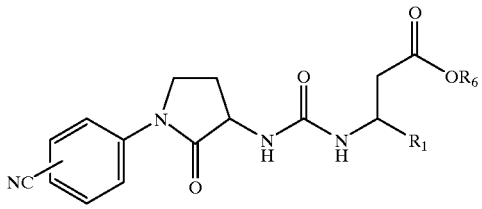

treating the urea with hydroxylamine to produce an aminodoxime, hydrogenating the amidoxime; and isolating a compound of the formula

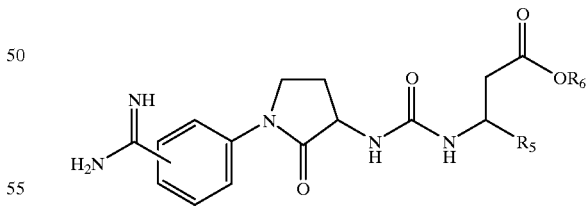

wherein R$_1$ is hydrogen, alkyl, aryl, arylalkyl, a heterocyclyl radical containing 1 to 3 heteroatoms or a heterocyclylalkyl and R$_6$ is selected from alkyl, aryl, arylalkyl or acyloxymethyl.

The process disclosed herein provides an efficient, scalable and cost effective synthesis of the intermediate (3S)-3-amino-1-(4-cyanophenyl)-2-oxopyrrolidine hydrochloride. The present process is advantageous over the process disclosed in U.S. Pat. No. 5,484,946 in that the process disclosed in U.S. Pat. No. 5,484,946 involved the coupling and acylization of a methionine residue which generated a great amount of dimethylsulfide. The cost associated with the waste handling of this by-product made the process unsuitable on a manufacturing scale. The presently disclosed process was designed to overcome this problem.

SUMMARY OF THE INVENTION

The present invention is directed to producing a lactam of the formula (I)

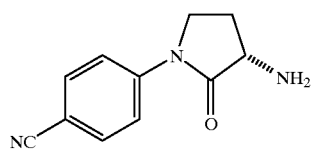

or a pharmaceutically acceptable salt thereof which process comprises coupling a compound of the formula (II)

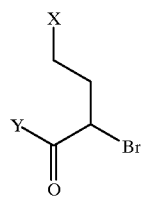

wherein X is Cl and Y is Br or X is Br and Y is Br with 4-aminobenzonitrile in THF or ACN, in the presence of propylene oxide or cyclohexene oxide or in the presence of a base selected from the group consisting of $Na_2HPO_4$, $Na_3PO_4$, $K_2CO_3$, $Na_2CO_3$ and $NEt_3$ to produce a compound of the formula (III)

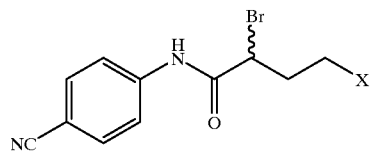

wherein X is Cl or Br;
adding sodium hydroxide or potassium hydroxide to the compound (III) so obtained to produce a compound of the formula (IV)

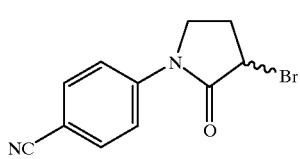

subjecting the compound of the formula IV to an excess of ammonium hydroxide to produce a compound of the formula (V)

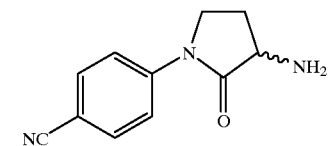

isolating the compound V and resolving the compound so isolated with salicylaldehyde or 3,5-dichlorosalicylaldehyde in a solvent selected from the group consisting of methanol, ethanol and isopropanol to produce a compound of the formula or a pharmaceutically acceptable salt thereof and isolating the compound so produced.

DETAILED DECRIPTION OF THE INVENTION

The invention herein relates to the process set forth above. More specifically the invention relates to the detailed Scheme set forth hereafter and the description and examples which follow.

The following non-limiting examples, schemes and descriptions describe and illustrate methods for carrying out the process of the present invention, as well as other aspects of the present invention, and the results achieved thereby in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes described in these examples can be used to perform the process of the present invention.

Unless otherwise indicated all starting materials and equipment employed were commercially available.

SCHEME I

Sythesis of the racemic amine

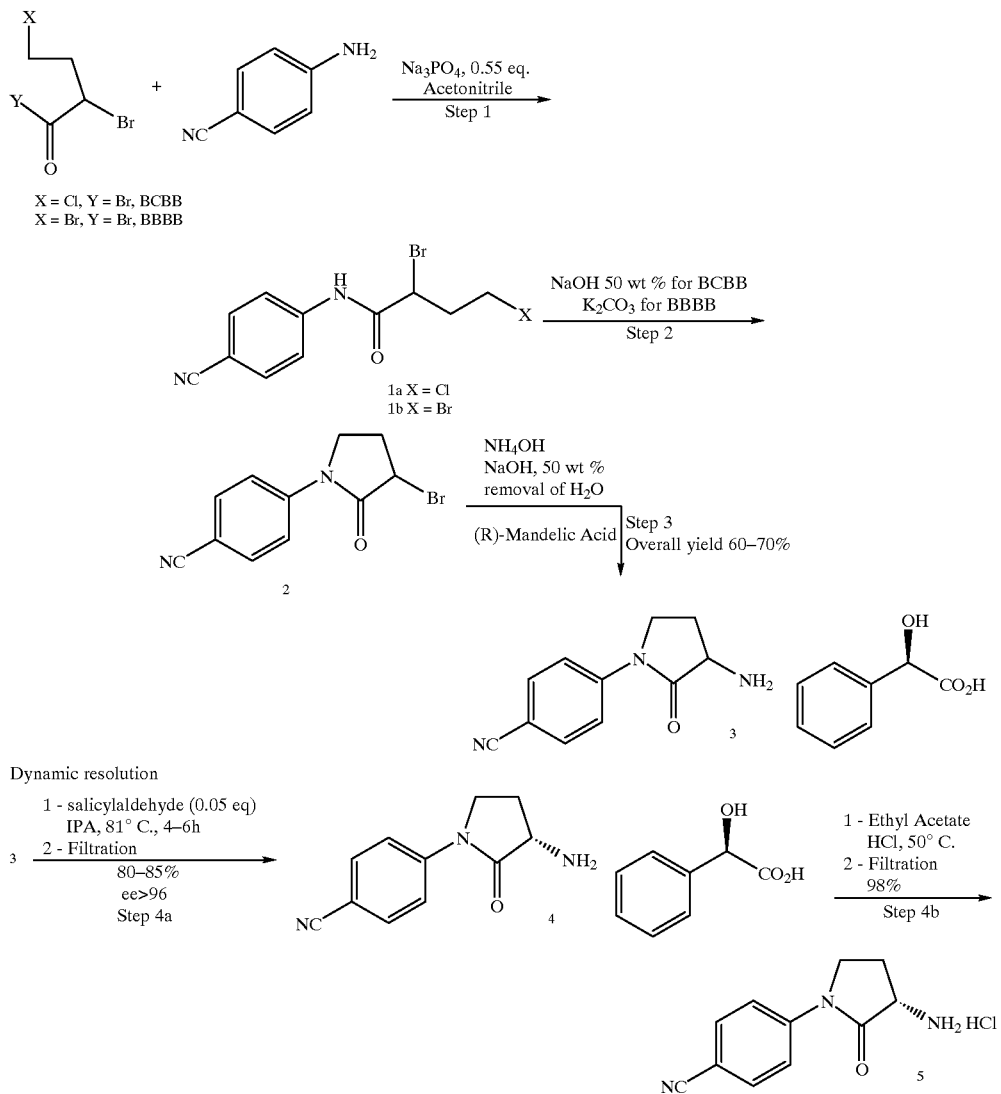

Dynamic resolution 2-bromo-4-halobutyryl halide and 4-aminobenzonitrile are coupled in THF or ACN, in the presence of propylene oxide or cyclohexene oxide or in the presence of a base like $Na_2HPO_4$, $Na_3PO_4$, $K_2CO_3$, $Na_2CO_3$ or $NEt_3$. The preferred conditions which could be effectively combined with the next 2 steps of the synthesis were obtained with $Na_3PO_4$ (0.55 equivalents) in acetonitrile to give a solution of 1a or 1b in acetonitrile.

The cyclization of 1a and 1b is then performed. For the cyclization of 1a, it was found that the addition of 50 wt. % aqueous sodium hydroxide (2.3 equivalents) to the reaction mixture solution led cleanly and rapidly to the bromolactam 2. Cyclization of 1 b was found to be best achieved by the addition of $K_2CO_3$ (2 equivalents) to the reaction mixture. Compound 2 was obtained as a solution in acetonitrile after filtration of the inorganic salts from either cyclization conditions. Aminolysis is achieved by subjecting 2 to a large excess of ammonium hydroxide. Thus, when the solution of compound 2 in acetonitrile is mixed with 17 equivalents of ammonia, the reaction proceeds smoothly at 40° C. in 6 hours. The work up of this reaction for the subsequent isolation of (racemic)-3 is achieved in the following way: distillation of acetonitrile and ammonium hydroxide, neutralization, azeotropic distillation with acetonitrile or toluene, and filtration of the inorganic salts. Addition of (R)-mandelic acid (MA) to the final solution leads to the precipitation of the salt (racemic)-3, which is isolated by filtration with an overall yield ranging from 60 to 70%. The dynamic resolution is achieved using the preformed salt (racemic)-3 and salicylaldehyde or 3,5-dichlorosalicylaldehyde as the aromatic aldehyde in alcohol solvents. Solvents such as methanol, ethanol or isopropanol (IPA) at their respective reflux temperature are suitable for achieving this type of transformation. The preferred results were found with IPA as the solvent, which gave the shortest reaction time and highest ee and salicylaldehyde, as it is easier to handle and more economic than 3,5-dichlorosalicylaldehyde. An excess of MA and a small amount of water results in shorter reaction time and higher optical purity of the isolated salt 4. The dynamic resolution which follows was found to be ineffective if a small amount of water was not included in the reaction. The preferred conditions (IPA at reflux temperature 3.25% $H_2O$, 7.75% excess MA); resulted in a high yield (78%) and high ee (>96%). The synthesis was completed by treatment of 4 with concentrated HCl in ethyl acetate at 50° C. for 1 hour to afford the desired product 5 in 98% yield. The present invention results in an easy and cost effective synthesis of the lactam molecule with high ee (>96%) and good overall yield (49%).

The following terms and abbreviations, as used herein have the meanings set forth below:

4-ABN=4-aminobenzonitrile
ACN=acetonitrile
DMF=dimethylformamide
EA=ethyl acetate
ee=enantiomeric excess
eq=equivalents
g=grams
GC=gas chromatography
GP or gp=glycoprotein
$^{13}$C-NMR=carbon 13 nuclear magnetic resonance
$^1$H-NMR=proton nuclear magnetic resonance
h=hours
HPLC=high performance liquid chromatography
IPA=isopropanol
IR=infrared
$K_2CO_3$=potassium carbonate
$NEt_3$=triethylamine
$Na_2CO_3$=sodium carbonate
$Na_2HPO_4$=disodium phosphate
NaOH=sodium hydroxide
$Na_3PO_4$=sodium phosphate
LC=liquid chromatography
MA=mandelic acid
MeOH=methanol
max=maximum
mL=milliliter
THF=tetrahydrofuran
TLC=thin layer chromatography
UV=ultraviolet
wt=weight

EXAMPLE 1

2-bromo-4-chlorobutyryl bromide

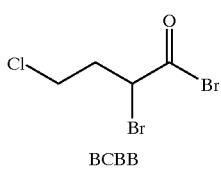

BCBB 4-chlorobutyryl chloride, bromine (200 mL, 8.88 moles) and HBr (2.5 mL, 0.028 mole, 48 wt % in water) were charged in a reactor under nitrogen. The solution was heated to 65° C. over 1 hour (ramping from 22° C. to 65° C.) and stirred for 8 hours while monitoring by GC. The mixture was then cooled to 22° C. and bromine (125 mL) was added followed by HBr (0.5 mL). The reaction mixture was heated to 65° C. over 1 hour (ramping from 22° C. to 65° C.) and stirred at 65° C. for 6 hours. The solution was then cooled to 22° C. and the temperature maintained for 16 hours. An extra portion of bromine (30 mL) and HBr (90.5 mL) was added and the mixture was heated and stirred for an extra 7 hours at 65° C. The excess of bromine and HCl was removed by house vacuum to afford a crude solution (1.57 Kg) containing a trace of non-brominated material (2–3% by GC) and some carboxylic acid (1–3%). The components of the crude product were determined by derivatization in MeOH [bromo butyrolactone (derivatization of 2-bromo-4-chlorobutyric acid), methyl 2-bromo-4-chlorobutyrate (derivatization of BCBB) and methyl 4-chlorobutyrate (derivatization of 4-chlorobutyryl chloride, starting material)].

Analytical method $Na_2CO_3$ (~170 mg), methanol (10 mL) and BCBB (170–200 mg) were added to a vial and stirred at room temperature for 30 minutes. The solution was filtered through a syringe filter (0.45 mL). The solution (1 mL) was diluted with acetonitrile to 10 mL.

The samples were compared and quantitated to a standard mixture of marker of bromo butyrolactone (derivatization of 2-bromo4-chlorobutyric acid), methyl 2-bromo4-chlorobutyrate (derivatization of BCBB) and methyl 4-chlorobutyrate (derivatization of 4-chlorobutyryl chloride, starting material).

GC method:

HP-1 column (crosslinked methyl siloxane), length: 10 m, ID: 0.53 mm, film thickness: 2.65 micron, phase ratio: 50, initial time: 2 minutes, initial temperature: 50° C., injector temperature: 180° C., detector temperature: 250° C., rate: 15° C./minute, final temperature: 170° C., final time: 0 minutes, run time: 10 minutes, injector volume: 1 mL.

Preparation of methyl 2-bromo4-chlorobutyrate

BCBB (100 g, 0.37 mole) was added via an addition funnel to MeOH (100 mL) in a 500 mL three neck, round bottom flask with a magnetic stirrer while maintaining the temperature at 20° C. with an ice bath. The mixture was stirred at 20–22° C. for 16 hours and concentrated under reduced pressure to afford an orange liquid (103.78 g). The crude product was filtered through $SiO_2$ (100 g) and eluted with a mixture of heptane and EA 9:1. The solution was concentrated to afford the desired material (75 g). The crude product was then purified by flash chromatography (300 g, $SiO_2$) elution heptane/EA) by collecting fractions (75 mL) and monitoring by TLC (Rf: 0.54, heptane/EA 10%). Fractions 5 through 11 were combined and concentrated under reduced pressure to afford the methyl 2-bromo4-chlorobutyrate as a colorless oil (66.02 g).

GC showed purity of 98.5%, contaminated with methyl 4-chlorobutyrate (1.5%).

$^1$H NMR ($CDCl_3$, TMS) (ppm) 2.38 to 2.53 (m, 2H), 3.67 to 3.75 (m, 2H), 3.81 (s, 3H), 4.54 (dd, 1 H, J=5.72, 8.76 Hz); $^{13}$C NMR ($CDCl_3$, TMS) (ppm) 36.90, 41.63, 42.22, 53.09, 169.49. Analysis calculated for $C_5H_8BrClO_2$: C, 27.87; H, 3.74; Br, 37.08; Cl, 16.45. Found: C, 28.26; H, 3.85; Br, 37.07; Cl, 16.21.

EXAMPLE 2
Solution of 4-(3'-bromo-2'-oxopyrrolidin-1'-yl)-benzonitrile in acetonitrile

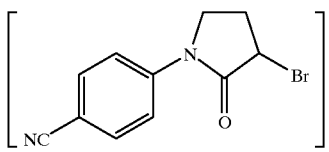

2-Bromo4-chlorobutyryl bromide (BCBB, 145.7 g, 0.540 mole) was added via an addition funnel to a cold (5° C.), well stirred slurry of 4-aminobenzonitrile (4-ABN, 55.0 g, 0.466 mole), $Na_3PO_4$ (42 g, 0.256 mole) and acetonitrile (550 mL) in a 1 liter flask while maintaining a temperature below 30° C. during the addition. The addition funnel was rinsed with acetonitrile (55 mL). Upon completion of the coupling (determined by LC), a 50 wt % solution of NaOH (56 mL, 1.061 mole) was added via an addition funnel while maintaining the reaction temperature below 30° C. Upon completion of the reaction (determined by LC), the slurry was filtered through a pressure filter (10 micron polypropylene filter cloth). The flask and the cake were washed with acetonitrile (256 mL). The filtrate and the wash were combined to afford a solution of 4-(3-bromo-2-oxopyrrolidin-1-yl)benzonitrile in acetonitrile (of about 17 wt %). Qualitative LC analysis showed the product with 91.8 to 95 area % purity.

LC method:
Synchropak RPP-100 (4.6 mm×25 cm); Gradient mobile phase: Solution A (0.05% trifluoroacetic acid in acetonitrile) and Solution B (0.05% trifluoroacetic acid in water); Gradient table: 0–1 min. 5% A/95% B; 30 min. 67% A/33% B; 31 min. 5% A/95% B. Flow Rate: 1 mL/minute; Injection Volume: 10 mL; Detection: 210 nm.

EXAMPLE 3
Solution of 4-(3'-bromo-2'-oxopyrrolidin-1'-yl)-benzonitrile in acetonitrile

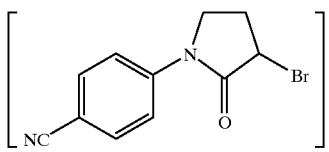

2,4-Dibromobutyryl bromide (BBBB, 12.13 g, 0.039 mole) was added via an addition funnel to a cold (5° C.), well stirred slurry of 4-aminobenzonitrile (4-ABN, 4.0 g, 0.034 mole), $Na_3PO_4$ (3.05 g, 0.019 mole) and acetonitrile (42 mL) while maintaining a temperature below 30° C. during the addition. The addition funnel was rinsed with acetonitrile (2 mL). Upon completion of the coupling (determined by LC), $K_2CO_3$ (9.36 g, 0.069 mole) was added via an addition funnel while maintaining the reaction temperature below 30° C. Upon completion of the reaction (determined by LC), the slurry was filtered. The flask and the cake were washed with acetonitrile (40 mL). The filtrate and the wash were combined to afford a solution of 4-(3-bromo-2-oxopyrrolidin-1-yl)benzonitrile in acetonitrile. Qualitative LC analysis showed the product with 96.1 area % purity.

EXAMPLE 4
(±) 4-(3'-Amino-2'-oxopyrrolidin-1'-yl)-benzonitrile (R)-mandelic acid salt (distillation procedure)

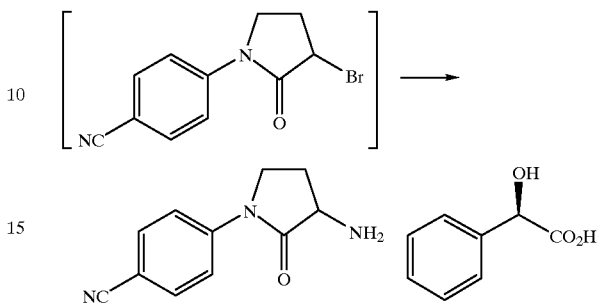

A 28 wt % aqueous solution of ammonia (495 g) was added to a solution of 4-(3-bromo-2-oxopyrrolidin-1-yl) benzonitrile in acetonitrile (estimated 17 wt %, 0.466 mole, theory). The mixture was slowly heated to 40° C. and stirred at that temperature for 6 hours and cooled to 22° C. upon completion (as determined by LC) to yield a hazy orange solution (1340 mL). Part of this solution (670 mL, 0.233 mole, theory) was used for the isolation. Ammonia and acetonitrile were distilled off from the reaction solution (670 mL, 0.233 mole) until the batch temperature reached 85° C. (400 mL of solvents collected). An aqueous solution of NaOH 50 wt % (18.4 g, 0.233 mole) was added to the distillation residue followed by toluene (500 mL). The wet toluene was distilled until the batch temperature reached 95° C. Toluene (400 mL) and water (85 g) were collected in the receiver and separated. The recovered toluene was recharged to the flask and distillation was resumed. The solvents were distilled until the temperature reached 95–97° C. Toluene (250 mL) and water (85 mL) were collected in the receiver. The reaction mixture was cooled to 50° C. and acetonitrile (350 mL) was added and the mixture was stirred for 16 hours at 22° C. The salts were then filtered off to afford a clear orange solution. The flask and solid were washed with acetonitrile (100 mL). (R)-Mandelic acid was then added at once to the combined filtrate and wash to precipitate the salt out of the solution. After 2.5 hours of stirring at 22° C., the slurry was filtered through a pressure filter and the flask and cake were washed with acetonitrile (150 mL). The cake was dried under vacuum at 50° C. to afford a white solid (52 g, 64% overall yield from 4-ABN) containing NaBr (0.42 wt %) and $H_2O$ (Karl Fisher analysis and calc'd 1.35 wt %).

$^1$H NMR (TMSD$_6$-DMSO) δ (ppm) 1.86 (m, 1H, 2.38 to 2.45 9 m, 1H), 3.73 to 3.86 (m, 1H), 3.4 to 5.5 (broad peak OH, NH$_2$, water); $^{13}$C NMR (TMS/D$_6$-DMSO) δ (ppm) 25.27; 44.44; 52.43; 72.94; 106.00; 118.79; 119.06; 126.40; 126.73; 127.63; 133.11; 142.02; 142.99; 173.30; 174.60; DSC 166.72° C. (107.3 J/g); Microanalytical: Calculated for C$_{19}$H$_{19}$N$_3$O$_4$ C: 64.58; H: 5.42; N: 11.89; Br: 0.00 Found C: 63.64; H: 5.24; N: 11.71; Br: 1.05. IR μ (cm−1) 2226, 1710.

EXAMPLE 5
(±) 4-(3'-Amino-2'-oxopyrrolidin-1'-yl)-benzonitrile (R)-mandelic acid salt (extraction procedure)

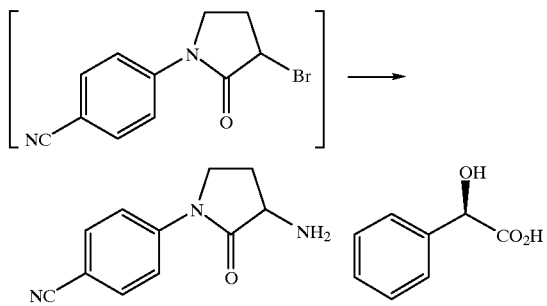

An aqueous solution (28 wt %) of ammonia (540 g) was added to a solution of 4-(3-bromo-2-oxopyrrolidin-1-yl) benzonitrile in acetonitrile (estimated 17 wt %, 0.466 mole, theory). The mixture was slowly heated to 40° C., stirred at that temperature for 6 hours and cooled to 22° C. upon completion (as determined by LC) to yield a hazy orange solution (1272 g). Part of this solution (1013 g, 0.373 mole, theory) was used for the work-up. NaCl (55 g) and an aqueous solution of NaOH (19.4 g, 0.376 mole, 50 wt %) were added to the reaction mixture at 10° C. The layers were separated and the aqueous layer was extracted twice with acetonitrile (2×250 mL). The three organic fractions were combined with an additional volume of acetonitrile (250 mL). The acetonitrile was distilled while adding fresh acetonitrile (500 mL). Wet acetonitrile (1035 mL) was collected in the receiver. The mixture was cooled to 22° C. and the salts were filtered off to afford a clear orange solution. The flask and solid were washed with acetonitrile (100 mL). (R)-Mandelic acid (47.6 g, 0.313 mole) was added at once to the combined filtrate and wash to precipitate the salt out of the solution. After 2 hours of stirring at 22° C., the slurry was filtered through a pressure filter and the flask and cake were washed with acetonitrile (100 mL). The cake was then dried under vacuum at 50° C. to afford a white solid (81.1 g, 62% overall yield from 4-ABN).

EXAMPLE 6
(±)-4-(2'-bromo-4'-chlorobutyrylamino)-benzonitrile

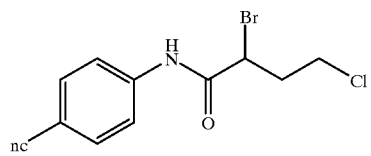

(±)-4-(2'-Bromo-4'-chlorobutyrylamino)-benzonitrile was purified as follows: a sample of reaction mixture was filtered and concentrated under reduced pressure. Upon concentration, some solid crystallized and was filtered. The solids (29.1 g) were taken up in toluene/THF (100/5 mL), heated to 70° C., cooled to 0° C. and filtered. The solids were washed with toluene (2×10 mL) and dried to afford a pale yellow solid (21.95 g). $^1$H NMR (CDCl$_3$, TMS) δ (ppm) 2.44 to 2.53 (m, 1H), 2.64 to 2.72 (m, 1H), 3.72 to 3.82 (m, 2H), 4.72 (dd, 1H, J=4.91, 8.97 Hz), 7.64 to 7.71 (m, 4H), 8.17 (s, 1H). $^{13}$C NMR (CDCl$_3$) δ (ppm) 37.16, 41.95, 46.60, 107.97, 118.59, 119.85, 133.35, 141.16, 166.40. IR μ (cm−1) 2228, 1692, 1602; Microanalytical: calculated for C$_{11}$H$_9$BrN$_2$O: C: 43.81; H: 3.34; N: 9.29; Br: 26.50; Cl: 11.76; found C: 42.85; H: 2.98; N: 9.13; Br: 25.52; Cl: 12.61.

EXAMPLE 7
(±)-4-(2',4'-bromobutyrylamino)-benzonitrile

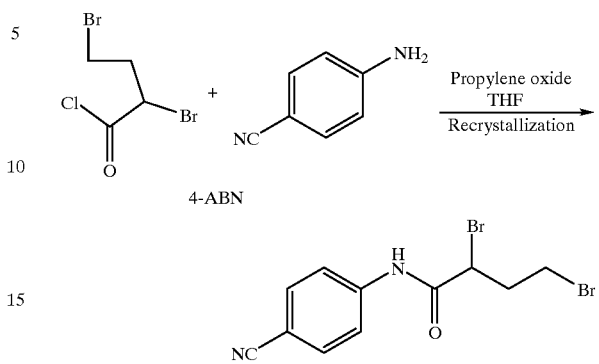

4-ABN

A 1L 3 port jacketed flask was charged with 4-aminobenzonitrile (31.4 g, 0.26 mole) and THF (technical grade, 225 mL). Stirring was started, the mixture vacuum/flushed with nitrogen and cooled to 0° C. (jacket set at −4° C.). 2,4-dibromobutyryl chloride (crude, 85% pure, 82.0 g, 0.26 mole) was added via a syringe after 30 minutes (exothermic, temperature rose to 9° C.) to form a slurry. After 20 minutes of stirring at 0° C., propylene oxide was added via a syringe (exothermic, temperature rose to 8° C.). The mixture was held at 22° C. and stirred for 2 hours at this temperature to form a homogeneous solution. The THF was removed under reduced pressure and toluene (250 mL) was added. After precipitation, the mixture was cooled to 5C and stirred for 16 hours at this temperature, filtered in a pressure filter, washed with toluene (50 mL) and dried under a flow of nitrogen and vacuum in the filter for 3 hours to afford the desired material (49.3 g). The mother liquor was concentrated to dryness (oily solid), taken up in toluene (125 mL) and THF (20 mL), recrystallized by heating to 50° C. (homogeneous solution) and cooled slowly to 2° C. The solution was filtered and the cake washed with toluene to afford additional material (15.09 g, total yield 72%).

$^1$H NMR (CDCl$_3$, TMS) δ (ppm) 2.52–2.61 (1H, m), 2.69–2.77 (1H, m), 3.62 (m, 1H), 4.72 (dd, 1H, J=4.9, 8.9 Hz), 7.66 (d, 2H, J=2.1 Hz), 7.69 (2H, J=2.1 Hz), 8.26 (1H, s); $^{13}$C NMR (CDCl$_3$) δ (ppm):30.30, 37.03, 47.52,107.71, 118.76, 119.99, 144.39, 141.44, 166.65; DSC: 136.73° C. (endo. 60.23 J/g), 221.59° C. (exo. 463.8J/g); IR (MIR) μ (cm−1) 2226, 1672, 1600, 1539; UV max (nm)=211(abs= 0.454); Rf=0.30 (EA45%/Heptane 55%); Microanalytical: calculated for C$_{11}$H$_{10}$Br$_2$N$_2$O: C: 38.18; H: 2.91; N:8.10; found: (first cake) C: 38.09; H: 2.93; N: 7.75; (second cake) C: 38.03; H: 2.83; N: 8.02.

EXAMPLE 8
(±)-4-(3'-bromo-2'-oxopyrrolidin-1'-yl)benzonitrile

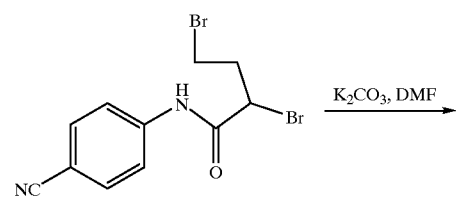

-continued

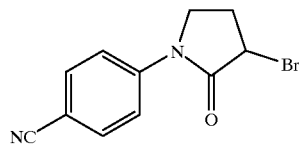

A well mixed slurry of $K_2CO_3$ (13.98 g, 0.1 mole), (±)-4-(2',4'-dibromobutyrylamino)benzonitrile (35.0 g, 0.1 mole) in DMF (90 mL) was heated under $N_2$ at 50° C. for 4 hours. After the mixture was cooled to 22° C., $H_2O$ (180 mL) was added while cooling to 10–15° C. with an ice bath. The slurry was stirred at 22° C. for 30 minutes and the solids were isolated by filtration, washed with $H_2O$ (2×30 mL) and dried on the filter with a flow of $N_2$ to afford the product (18.89 g).

$^1$H NMR (CDCl$_3$, TMS) δ (ppm) 2.46 to 2.53 (m, 1H), 2.71 to 2.81 (m, 1H), 3.84 to 3.89 (m, 1H), 4.04 to 4.11 (m, 1 H), 4.6 (d-d, 1H, J=2.9, 7.0 Hz), 7.68 (d, 2H, J=9.0 Hz), 7.83 (d, 2H, 9.0); $^{13}$C NMR δ (CDCl$_3$) (ppm): 29.65, 44.53, 46.26, 108.15, 118.54, 119.54, 133.09, 142.61, 170.09; DSC: 115.24° C. (endo. 69.07 J/g), 213.55° C. (exo. 148.6 J/g); IR (MIR) (cm−1) 2224, 1704, 1602, 1510; UV max (nm)=203 (abs=0.503), 213 (abs=0.541), 278 (abs=0.782); Rf=0.13 (EA 45%/Heptane 55%); Microanalytical: calculated for $C_{11}H_9BrN_2O$: C: 49.84; H: 3.42; N: 10.57; Br: 30.14; found: C: 50.02; H: 3.63; N: 10.52; Br: 29.71.

EXAMPLE 9

(−)-(3'S)-4-(3'-Amino-2'-oxopyrrolidin-1'-yl)-benzonitrile (R)-mandelic acid salt

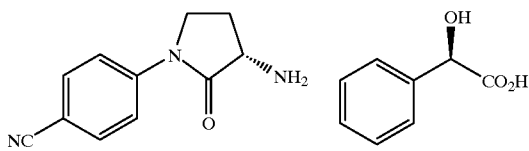

(R)-mandelic acid (0.23 g, 1.5 mmole), water (0.39 g) and salicylaldehyde (0.05 mL, 0.42 mmoles) were added to a slurry of racemic (±) 4-(3-amino-2-oxopyrrolidin-1-yl) benzonitrile (R)-mandelic acid salt (3.0 g, 8.49 mmoles) in IPA (12 mL). The slurry was heated to reflux, stirred for 24 hours and monitored by chiral HPLC. [Method: Crownpak CR (−) column (15 cm×4.6 mm), isocratic mobile phase: 5% MeOH/95% 7% aq. HClO$_4$], 1=280 nm, retention times for R and S enantiomers=14.7 and 19.6 minutes, respectively). The slurry was cooled to 22° C. and filtered. The solids were washed with IPA (3.5 mL) and dried to afford a white powder (2.34 g, 78% yield) 98.7% S enantiomer as determined by chiral HPLC; >99% pure by achiral HPLC [Method: Synchropak SCD-100 column (25 cm×4.6 mm), gradient mobile phase: A=5% trifluoroacetic acid in water and B=5% trifluoroacetic acid in acetonitrile; gradient table; 0–0.2 minutes 95%A/5%B, 30 minutes 33%A/67%B, 30.5 minutes 95%A/5%B]. $[\alpha]_{365}$=−66.2 (c=1.01, DMSO). Mp: 177° C. IR (cm$^{-1}$) 2222, 1730. $^1$H NMR (400 MHz, DMSO-d$_6$): δ 1.87 (1H, dq, J=12.2, 9.8 Hz), 2.41 (1H, dddd, J=12.2,8.4,6.7,1.7 Hz), 3.76 (1H, td, J=10.6, 8.4 Hz), 3.83 (1H, td, J=9.4, 1.7 Hz), 4.81 (1H,s), 7.22 (1H, tt, J=7.2,1.6 Hz), 7.28 (2H, complex t, J~7.3 Hz), 7.38 28 (2H, complex d, J~7.5 Hz), 7.86 28 (2H, complex d, J~9.1 Hz), 7.91 28 (2H, complex d, J~9.1 Hz). $^{13}$C NMR (500 MHz, DMSO-d$_6$): δ 25.24, 44.44, 52.41, 72.97, 106.01, 118.80, 119.06, 126.40, 126.70, 127.63, 133.11, 142.09, 142.98, 173.26, 174.65.

Analysis calculated for $C_{19}H_{19}N_3O_4$: C, 64.58; H, 5.42; N, 11.89. Found: C, 64.42; H, 5.44; N, 11.92.

EXAMPLE 10

(−)-(3'S)-4-(3'-Amino-2'-oxopyrrolidin-1'-yl)benzonitrile hydrochloride salt

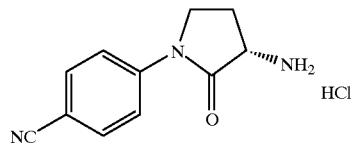

Concentrated HCl (70.7 mL, 0.85 mole) was added to a slurry of the product of Example 9 (200.0 g, 0.57 mole) in ethyl acetate (1.2 L). The mixture was heated to 50° C. and stirred for 1 hour. The slurry was cooled to 24° C. and filtered. The solid was washed with ethyl acetate (1×200 mL) and dried in a vacuum oven at 60° C. to afford the desired product as a white powder (131.2 g, 97.5% yield) 98.0% S enantiomer as determined by chiral HPLC. [Method: Crown Pak (−) column (15 cm×4.6 mm), 35° C., isocratic, mobile phase: 5% MeOH/95% 7% aqueous HClO$_4$, 1=280 nm, retention times for R and S enantiomers= 10.8 and 14.7 minutes respectively]. Purity 99.9% by achiral HPLC [Method: Synchropak SCD-100 column (25 cm×4.6 mm), gradient mobile phase: A=5% trifluoroacetic acid in water and B=5% trifluoroacetic acid in acetonitrile; gradient table; 0–0.2 minutes 95%A/5%B, 30 minutes 33%A/67%B, 30.5 minutes 95%A/5%B]. $[\alpha]_{365}$=−66.2 (c=1.05, H$_2$O).

Mp: 272° C. IR (cm$^{-1}$) 2226, 1708. $^1$H NMR (400 MHz, DMSO-d$_6$): δ 2.15 (1H, ddt, J=12.0, 10.8, 9.7 Hz), 2.54 (1H, dddd, J=12.0, 8.8, 6.8, 1.0 Hz), 3.87 (1H, td, J=9.7, 6.8 Hz), 3.97 (1H, td, J=9.7, 1.0 Hz), 4.27 (1H, dd, J=10.8, 8.8 Hz), 7.91 (4H, s), 8.73 (3H, br s). $^{13}$C NMR (500 MHz, DMSO-d$_6$): d 23.17, 44.82, 51.13, 106.52, 118.67, 119.31, 133.22, 142.49, 169.97;. Analysis calculated for $C_{11}H_{12}ClN_3O \cdot 0.25$ mol $H_2O$: C, 54.50; H, 4.95; Cl, 14.45; N, 17.34. Found: C, 54.67; H, 5.15; Cl, 14.51; N, 17.37.

What is claimed is:

1. A process for producing a lactam of the formula (I)

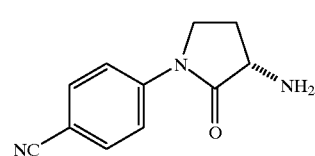

or a pharmaceutically acceptable salt thereof which process comprises coupling a compound of the formula (II)

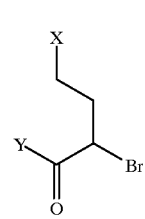

wherein X is Cl and Y is Br or X is Br and Y is Br with 4-aminobenzonitrile in THF or ACN, in the presence of propylene oxide or cyclohexene oxide or in the presence of a base selected from the group consisting of Na$_2$HPO$_4$, Na$_3$PO$_4$, K$_2$CO$_3$, Na$_2$CO$_3$ and NEt$_3$ to produce a compound of the formula

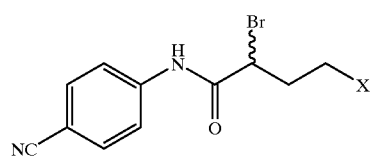

(III)

wherein X is Cl or Br;
adding sodium hydroxide, potassium hydroxide or potassium carbonate to the compound (III) to produce a compound of the formula

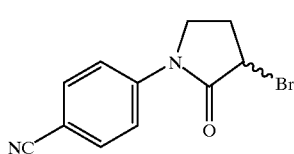

(IV)

subjecting the compound of the formula IV to an excess of ammonium hydroxide to produce a compound of the formula

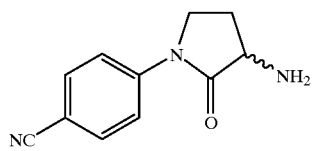

(V)

isolating the compound V or a pharmaceutically acceptable salt thereof and resolving the compound so isolated with salicylaldehyde or 3,5-dichlorosalicylaldehyde in a solvent selected from the group consisting of methanol, ethanol and isopropanol to produce a compound of the formula

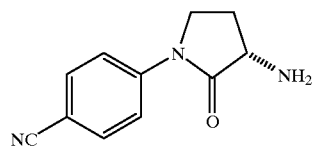

and isolating the compound or a pharmaceutically acceptable salt thereof so produced.

* * * * *